United States Patent
Seo et al.

(10) Patent No.: US 8,706,204 B2
(45) Date of Patent: Apr. 22, 2014

(54) SYSTEM AND METHOD FOR OBSERVING HEART RATE OF PASSENGER

(71) Applicants: Hyundai Motor Company, Seoul (KR); Kia Motors Corp., Seoul (KR)

(72) Inventors: Sang Man Seo, Ansan-si (KR); Gil Ju Kim, Hwaseong-si (KR); Tae Hyoung Yang, Seoul (KR); In Ho Lee, Hwaseong-si (KR); Hee Chan Kim, Seoul (KR); Seung Woo Noh, Seoul (KR); Chi Yul Yoon, Seoul (KR)

(73) Assignees: Hyundai Motor Company, Seoul (KR); Kia Motors Corp., Seoul (KR); Hyundai Dymos Incorporated, Seosan-Si (KR); SNU R&DB Foundation, Seoul (KR)

( * ) Notice: Subject to any disclaimer, the term of this patent is extended or adjusted under 35 U.S.C. 154(b) by 0 days.

(21) Appl. No.: 13/682,468

(22) Filed: Nov. 20, 2012

(65) Prior Publication Data

US 2014/0039330 A1     Feb. 6, 2014

(30) Foreign Application Priority Data

Aug. 3, 2012    (KR) .................. 10-2012-0085070

(51) Int. Cl.
*A61B 5/04*      (2006.01)

(52) U.S. Cl.
USPC ............................................. 600/509

(58) Field of Classification Search
USPC ............................................. 600/509
See application file for complete search history.

(56) References Cited

U.S. PATENT DOCUMENTS

| | | | | |
|---|---|---|---|---|
| 7,379,770 | B2 * | 5/2008 | Szeto ........................ | 600/519 |
| 7,684,854 | B2 * | 3/2010 | Park et al. ................. | 600/509 |
| 2006/0283652 | A1 * | 12/2006 | Yanai et al. ................ | 180/272 |

FOREIGN PATENT DOCUMENTS

| | | |
|---|---|---|
| JP | 2011-24902 A | 2/2011 |
| KR | 10-0736721 B1 | 7/2007 |

* cited by examiner

*Primary Examiner* — George Manuel
(74) *Attorney, Agent, or Firm* — Morgan, Lewis & Bockius LLP

(57) ABSTRACT

A system and method is provided for observing a heart rate of a passenger. The system for observing a heart rate of a passenger includes a plurality of different types of heart rate sensors provided on a seat cushion or a seat back, and a control unit for collecting waveforms of the heart rate sensors for respective sensor types, computing accuracies of the waveforms for respective sensor types at each unit time, selecting a waveform having a highest accuracy at each unit time, and then calculating a heart rate.

10 Claims, 4 Drawing Sheets

SYSTEM AND METHOD FOR OBSERVING HEART RATE OF PASSENGER

CROSS-REFERENCE TO RELATED APPLICATION

The present application claims priority of Korean Patent Application Number 10-2012-0085070 filed Aug. 3, 2012, the entire contents of which application is incorporated herein for all purposes by this reference.

BACKGROUND OF INVENTION

1. Field of Invention

The present invention relates to a system and method for observing the heart rate of a passenger, which can exactly measure the heart rate of a passenger and provide a health care service corresponding to the measured heart rate.

2. Description of Related Art

Research into technology for providing health, safety and convenience services based on biometric signals in a vehicle has been active. The demand for measurement technology that measures various biometric signals, especially, the heart rate, has increased. The reason for this is that the heart rate of a passenger reflects both the physical and mental state of the passenger, so that the heart rate may be a basis for the provision of new services.

Various heart rate sensing methods in a vehicle environment have been evaluated. Representatives sensing methods include an electrocardiogram (ECG), a ballistocardiogram (BCG), a phonocardiogram (PCG), a photoplethysmogram (PPG), etc. These methods sense the heart rate using different principles. In a series of procedures in which a heart beat starts at the stimulation of a heart muscle cell and causes variations in a blood flow, electrical, mechanical, and optical signals are generated, so that the heart rate can be detected using various methods.

However, to date, none of the above methods have so far been applied to actual vehicles. The most difficult thing is that a relatively weak heart rate signal is easily contaminated by noise sources, such as vibration noise or the motion of a passenger, due to the influence of various environment variables present in the vehicle environment. As a result, the period of an available heart rate signal is shortened, so that the shape of the signal discontinuously appears, thus causing a decrease in the amount of extractable information.

This problem may be solved by employing a method that uses a combination of different sensors immune to specific environment variables, juxtaposes the sensors at various locations, and then recombines the signals. The present invention is intended to present such a method. This method enables the heart rate to be more robustly sensed in a vehicle compared to a single sensor-based measurement, so that the state of the passenger can be easily analyzed. In addition, a larger amount of information about the state of the passenger can be extracted by comparing the synchronization information between individual signals. Feedback suitable for the state of each individual person is provided based on the extracted state information, thus promoting the safety and convenience of the passenger with higher performance.

For example, JP 2011-024902 A presents a technology for selecting a single measurement result from among a plurality of measurement results and taking ECG measurements, but it is merely configured to make a simple comparison based on the amplitude or Signal to Noise (S/N) ratio and select any one signal. Accordingly, this technology is actually insufficient for application to a technology for stably measuring, evaluating, and selecting various types of signals related to the heart rate.

Further, KR 0736721 B also presents a technology for installing sensors at locations corresponding to the shoulders and the hips, filtering noise, and amplifying the filtered signals. However, this technology is problematic in that a lot of time is required by the procedure of filtering noise, and the accuracy of measurement is also deteriorated.

The information disclosed in this Background section is only for enhancement of understanding of the general background of the invention and should not be taken as an acknowledgement or any form of suggestion that this information forms the prior art already known to a person skilled in the art.

SUMMARY OF INVENTION

Accordingly, the present invention has been made keeping in mind the above problems occurring in the prior art. Various aspects of the present invention provide for a system and method for observing the heart rate of a passenger, which periodically evaluate and select the most suitable signal among a plurality of signals for a plurality of different types of sensors and even for the same type of sensor, thus stably obtaining a relatively accurate heart rate.

Various aspects of the present invention provide for a system for observing a heart rate of a passenger, including a plurality of different types of heart rate sensors provided on a seat cushion or a seat back; and a control unit for collecting waveforms of the heart rate sensors for respective sensor types, computing accuracies of the waveforms for respective sensor types at each unit time, selecting a waveform having a highest accuracy at each unit time, and then calculating a heart rate.

The heart rate sensors may include electrocardiogram (ECG) sensors.

The ECG sensors may be configured such that respective pairs of ECG sensors are provided on the seat back and the seat cushion.

The control unit may configure a plurality of ECG measurement circuit leads by combining the plurality of ECG sensors, thus deriving a plurality of waveforms related to the ECG.

The control unit may measure magnitudes of an R-peak and a P-peak of each waveform related to the ECG, and selects a waveform, in which a magnitude of an R-peak is five times or more as large as that of a P-peak, as a representative ECG waveform.

The control unit may measure magnitudes of an R-peak and a T-peak of each waveform related to the ECG, and select a waveform, in which a magnitude of an R-peak is three times or more as large as that of a T-peak, as a representative ECG waveform.

The heart rate sensors may include ballistocardiogram (BCG) sensors.

The BCG sensors may be individually provided on the seat back and on the seat cushion.

The BCG sensors may be configured such that a plurality of BCG sensors are provided, and the control unit may derive a plurality of waveforms related to the BCG for respective BCG sensors, compare a magnitude of an I-J signal with a magnitude of a noise signal for each waveform, and select a waveform, in which a magnitude of an I-J signal is seven times or more as large as that of a noise signal, as a representative BCG waveform.

The heart rate sensors may include phonocardiogram (PCG) sensors.

The PCG sensors may be provided on the seat back.

The PCG sensors may be configured such that a plurality of PCG sensors are provided in series on the seat back in a vertical direction.

The PCG sensors may be configured such that a plurality of PCG sensors are provided, and the control unit may derive a plurality of waveforms related to the PCG for respective PCG sensors, compare a maximum amplitude of a first cardiac sound with a magnitude of a noise signal for each waveform, and select a waveform, in which a maximum amplitude of a first cardiac sound is five times or more as large as that of a noise signal, as a representative PCG waveform.

The PCG sensors may be configured such that a plurality of PCG sensors are provided, and the control unit may derive a plurality of waveforms related to the PCG for respective PCG sensors, compare a maximum amplitude of a second cardiac sound with a magnitude of a noise signal for each waveform, and select a waveform, in which a maximum amplitude of a second cardiac sound is three times or more as large as that of a noise signal, as a representative PCG waveform.

The heart rate sensors may include photoplethysmogram (PPG) sensors.

The PPG sensors may be provided in a portion of the seat cushion coming into contact with thighs of the passenger.

The PPG sensors may be configured such that a plurality of PPG sensors are provided, and the control unit may derive a plurality of waveforms related to the PPG for respective PPG sensors and select a waveform having a largest number of frequency components ranging from 0.5 to 2 Hz, from among the plurality of waveforms, as a representative PCG waveform.

Each of the different types of heart rate sensors may measure signals related to the heart rate using a mechanical, electrical, or optical method.

The heart rate sensors may be provided such that a plurality of heart rate sensors are provided for respective sensor types, and the control unit may select representative waveforms for respective types of the heart rate sensors, compute accuracies of the selected waveforms at each unit time, select a waveform having a highest accuracy at each unit time, and then calculate a heart rate.

The present invention provides a method of observing a heart rate of a passenger, including collecting waveforms from a plurality of different types of sensors provided on a seat cushion or a seat back, for respective sensor types; computing accuracies of the waveforms for respective sensor types at each unit time; selecting a waveform having a highest accuracy at each unit time; and calculating a heart rate based on the selected waveform.

According to the system and method for observing the heart rate of a passenger having the above configuration, there is an advantage in that for a plurality of different types of sensors and even for the same type of sensor, the most optimal signal among a plurality of signals is periodically evaluated and selected, thus reliably obtaining a relatively accurate heart rate.

The methods and apparatuses of the present invention have other features and advantages which will be apparent from or are set forth in more detail in the accompanying drawings, which are incorporated herein, and the following Detailed Description, which together serve to explain certain principles of the present invention.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention (s) is/are intended to cover not only the exemplary embodiments, but also various alternatives, modifications, equivalents and other embodiments, which may be included within the spirit and scope of the invention as defined by the appended claims.

Figure 1:
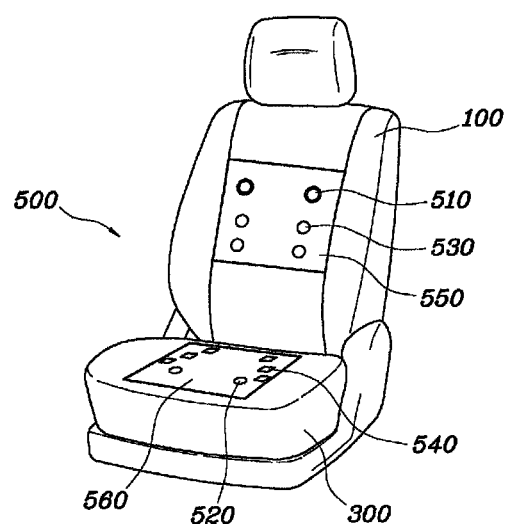
FIG. 1 is a diagram showing the arrangement of sensors of an exemplary system for observing the heart rate of a passenger according to the present invention.
Figure 3:
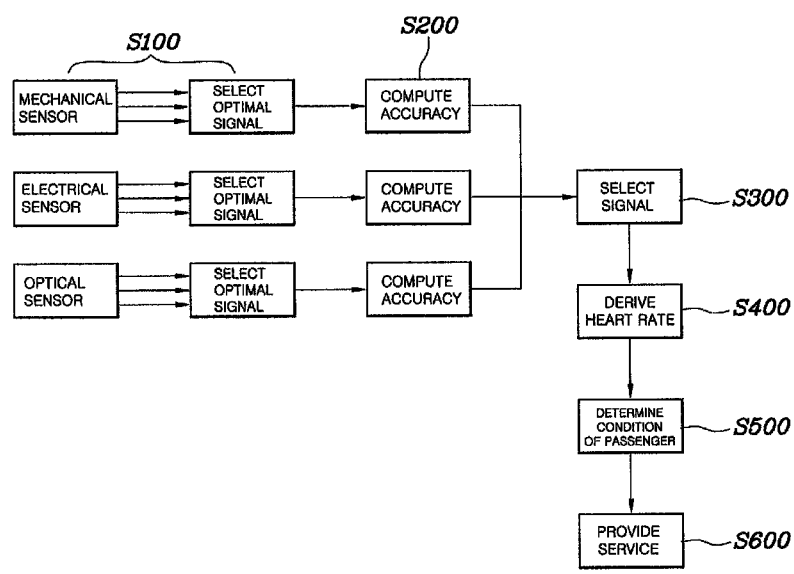
FIG. 3 is a flowchart showing an exemplary method of observing the heart rate of a passenger according to the present invention.

FIG. 1 is a diagram showing the arrangement of sensors of a system for observing the heart rate of a passenger according to various embodiments of the present invention, and FIG. 3 is a flowchart showing a method of observing the heart rate of a passenger according to various embodiments of the present invention.

The system for observing the heart rate of a passenger according to the present invention includes a plurality of different types of heart rate sensors 500 provided on a seat cushion 300 or a seat back 100; and a control unit for collecting waveforms of the heart rate sensors 500 for respective sensor types, computes the accuracies of the waveforms for respective sensor types at each unit time, selects a waveform having the highest accuracy at each unit time, and then calculates a heart rate based on the selected waveform.

The heart rate sensors are implemented as a combination of a plurality of sensors capable of measuring the heart rate using various methods, so that the heart rate sensors can be selectively applied to optimal locations on the seat back or the seat cushion of a seat.

Such different types of heart rate sensors 500 can individually measure signals related to the heart rate using mechanical, electrical, or optical methods.

Representative embodiments of the methods may include the electrocardiogram (ECG), ballistocardiogram (BCG), phonocardiogram (PCG), and photoplethysmogram (PPG).

As a method of obtaining an electrical signal, there is an ECG which is a method of measuring the voltage generated when the heart muscle is activated at two extracorporeal points.

Furthermore, as a method of obtaining an optical signal, there is a PPG which is a method of measuring variations in the amount of blood at an end-organ using variations in the amount of received light.

Furthermore, as a method of obtaining a mechanical signal, there are a BCG which is a method of measuring the reaction to the ejection of blood when the heart ejects the blood, and a PCG which is a method of measuring sounds, caused by vibrations created when the valves of the heart open and close, at extracorporeal locations.

All of the various medical methods are suitable for the derivation of the heart rate, and measurement technology for the methods has already been developed.

Meanwhile, such signals are synchronized with one another according to a specific time difference. The degree of the time difference is influenced by various physiological variables, such as the elasticity of a blood vessel or a blood pressure.

In detail, the ECG can be measured in a non-restrained measurement manner using a circuit that is capable of measuring the potential difference between two positions of the body and capacitive electrodes that are embedded in the seat. The BCG can be measured by disposing sensors, capable of measuring pressure or weight, between a human being and a seat frame. The PCG can be measured by bringing a stethoscope into close contact with the surface of the skin around the heart and by recording sounds using the stethoscope. The PPG can be measured in such a way as to emit light to a blood vessel around the skin using a sensor implemented as a pair of a light emitting unit and a light receiving unit, and measure the amount of light reflected by (or passed through) the blood vessel.

However, there may be distortion in the signals when the state of a contact between a driver and the sensors is not stable or when there is external noise, and thus a new method of smoothly obtaining signals is required.

That is, there are various environment variables that deteriorate coupling between the sensor and the human body. Also, there are situations in which the output of the sensor becomes inferior under some specific environmental condition.

Therefore, a scheme for overcoming such disadvantages is to use a combination of different types of heart rate sensors. The reason for this is that their sensitivities to respective environment variables differ depending on the type of sensor.

The following Tables show an example of differences between the sensitivities of the sensors and an example in which different types of sensors are used in combination.

TABLE 1

|  | Humidity | Clothing thickness | Sitting posture |
|---|---|---|---|
| ECG | Very sensitive | Slightly sensitive | Insensitive |
| PCG | Insensitive | Very sensitive | Slightly sensitive |
| BCG | Insensitive | Insensitive | Sensitive |
| PPG | Insensitive | Slightly sensitive | Insensitive |

TABLE 2

|  | Cushion | Seat back |
|---|---|---|
| ECG | Contact surface with left and right thighs | Contact surface with left and right lumbar vertebrae |
| PCG | N/A | Center portions of thoracic curves |
| BCG | Contact surface with hips | Left and right regions of back |
| PPG | Contact surface with thighs | N/A |

FIG. 1 illustrates the locations at which individual sensors are installed, which will be described in detail for respective sensors.

Meanwhile, the control unit collects the waveforms of the heart rate sensors 500 for respective sensor types, computes the accuracies of the waveforms for respective sensor types at each unit time, selects a waveform having the highest accuracy from among the waveforms at each unit time, and then calculates the heart rate based on the selected waveform. For this operation, the heart rate sensors 500 are implemented as a plurality of sensors for each type. The control unit can select representative waveforms for respective types of the heart rate sensors, compute the accuracies of the selected waveforms at each unit time, select a waveform having the highest accuracy at each unit time, and calculate a heart rate based on the selected waveform.

Figure 2:
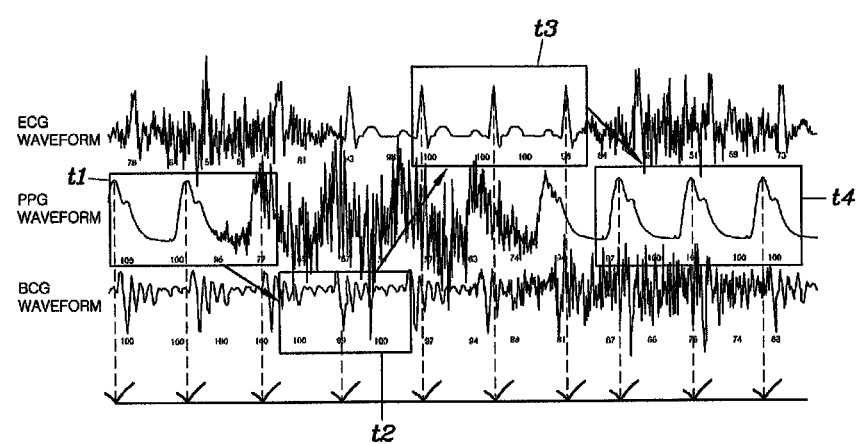
FIG. 2 is a graph showing a process for evaluating and selecting heart rates in the system for observing the heart rate of a passenger shown in FIG. 1.

That is, as shown in FIG. 2, the control unit evaluates waveforms for each type of sensor. Criteria for the evaluation may include items, such as whether each signal has been saturated, whether a base line is wandering, the degree of distortion of waveforms, the comparison of energy in a frequency domain, and signal energy in a time domain.

As shown in the example in the drawing, evaluation is performed at each unit time, such as t1, t2, and t3. For example, when at t1, it is determined that the waveform of a PPG has the highest accuracy, at t2, it is determined that the waveform of a BCG has the highest accuracy, at t3, it is determined that the waveform of an ECG has the highest accuracy, and at t4, it is determined that the waveform of a PPG has the highest accuracy, the heart rates are respectively calculated using the different waveforms at respective unit times. Further, since this calculation procedure uses the results of calculation while shifting waveforms, more accurate results can be obtained if time differences that may occur at the moment at which each waveform shifts (a shifting time point) are corrected.

Meanwhile, it is also possible to provide, as such sensors, a plurality of sensors for each sensor type, and use a waveform derived by an optimal sensor from among the sensors as the representative waveform of the corresponding type of sensor.

For example, the heart rate sensors 500 may include ECG sensors 510. The ECG sensors 510 may be provided such that respective pairs 510 and 520 of ECG sensors are provided on the seat back 100 and the seat cushion 300, and the control unit configures a plurality of ECG measurement circuit leads by combining the plurality of ECG sensors 510, thus deriving a plurality of waveforms related to the ECG.

Further, the control unit may measure the magnitudes of the R-peak and the P-peak of each waveform related to the ECG, and select a waveform, in which the magnitude of an R-peak is five times or more as large as that of a P-peak, as the representative ECG waveform. Alternatively, the control unit may measure the R-peak and the T-peak of each waveform related to the ECG and select a waveform, in which the magnitude of an R-peak is three times or more as large as that of a T-peak, as the representative ECG waveform.

Figure 4:
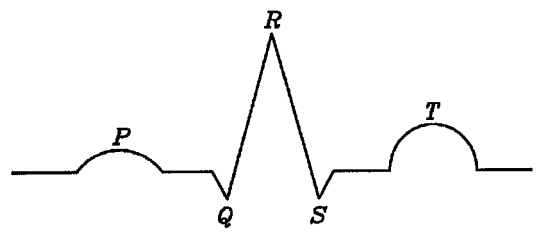
FIG. 4 is a graph showing the waveform of a theoretical ECG.

FIG. 4 is a graph showing the waveform of a theoretical ECG. That is, the ECG sensors must be implemented as at least a pair (two sensors) so as to measure a single signal, and at least two pairs of sensors are located in a back contact portion and a hip contact portion of the seat, respectively. Accordingly, when the contact position has changed due to a variation in the posture of the passenger, combinations of different sensors can be selected.

It is possible to implement nC2 combinations depending on the combination of selecting two sensors from among n sensors, and configure individual leads of the ECG. Since the strength of the contact between the sensors located in individual portions of the seat and the surface of the body varies according to the posture of an examinee (passenger), the state of contact of the individual sensors is determined in real time, and leads from which signals are expected to be desirably output are selected.

In order to evaluate the basic signal qualities of the selected leads, the magnitudes of the R-peak, P-peak, and T-peak of each signal are measured. The ratios of the magnitudes of the peaks are calculated, and signals suitably satisfying the ratios of R-peak and P-peak of 5:1 or more and the ratios of R-peak and T-peak of 3:1 or more are selected and defined as high-quality signals, and the optimal ECG signal is selected from among the defined ECG signals.

For reference, an electrocardiogram, that is, the ECG, is a graph of active current obtained by measuring at two extracorporeal points the current that flows when a heart muscle is activated. The ECG is widely applied to the fields of diagnosis of various types of arrhythmia or electrolytic disorders, or the examination and verification of the existence of abnormalities of the heart while performing an operation, as well as coronary diseases such as the stricture of the heart or myocardial infarction, and is very important to the diagnostics of cardiac diseases.

Heart Rate Variability (HRV) is an index required to measure the time intervals between the R-peaks of the ECG and check physiological conditions. For a normal person, a variation in the R-R peak interval occurs because the autonomic nervous system antagonizes the part that generates the heart rhythm. Therefore, when the variation in the R-R peak interval is analyzed, the activity of the sympathetic/parasympathetic nervous systems constituting the autonomic nervous system can be detected. The activity of the sympathetic/parasympathetic nervous systems is well known as one of the sensitive variables that desirably reflect the stressed condition of the body.

Figure 5:
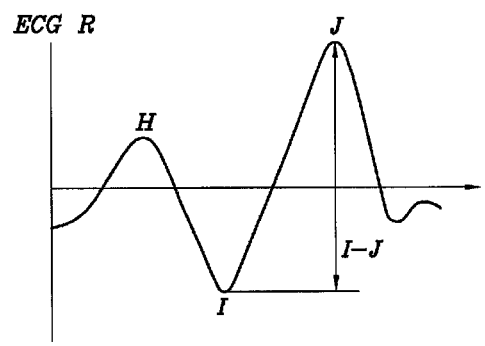
FIG. 5 is a graph showing the waveform of a theoretical BCG.

Meanwhile, FIG. 5 is a graph showing the waveform of a theoretical BCG. The heart rate sensors 500 may include BCG sensors 550.

The BCG 550 may be individually provided on the seat back 100 and on the seat cushion 300, as indicated by reference numerals 550 and 560. A plurality of BCG sensors 550 are provided, and the control unit can derive a plurality of waveforms related to the BCG for respective BCG sensors 550, compare the magnitude of an I-J signal with the magnitude of a noise signal for each waveform, and select a waveform, in which the magnitude of an I-J signal is seven times or more as large as that of a noise signal, as the representative BCG waveform.

As the BCG sensors, sensors implemented as piezoelectric elements are disposed in a hip contact portion because the principle of the BCG is based on the repulsive power with which the blood flow is ejected from the heart. The output waveform of the BCG may vary according to the state of contact between the examinee and the surfaces of the sensors because the angles between a blood vessel and the BCG sensors differ according to the posture of a user (the examinee). Four (2*2 array) or more BCG sensors are disposed in the hip contact portion, so that signals can be obtained in accordance with variations in the posture of the examinee, differences in the location of contact attributable to the center of gravity of the body of the examinee, etc. In the case of each BCG signal, the magnitude of an I-J signal is compared with a noise level, so that BCG signals in which the magnitude of an I-J signal is seven times or more as large as a noise level are defined as high-quality signals, and an optimal BCG signal is selected from among the high-quality signals.

For reference, the BCG refers to a ballistocardiogram that is a method of, when the heart ejects blood, measuring a reaction to the ejection, and then estimating the state of the heart. This BCG is obtained by directly measuring a fine variation in acceleration or a variation in the weight of the body, caused by the reaction to the ejection of a blood flow, and is intended to determine the magnitudes, time intervals, or gradients of the signals. Among these items, the magnitude of the I-J signal is used as the most principal target of analysis.

In the BCG signal over time indicated based on the R-peak of the ECG waveform, I denotes a signal output when the heart ejects blood through the main artery, and J denotes a signal output when blood moves down to the lower part of the body, wherein the contractile force of the left ventricle can be estimated using the magnitude of the I-J signal.

Meanwhile, the heart rate sensors 500 may include PCG sensors 530. The PCG sensors 530 are provided on the seat back 100. In particular, a plurality of PCG sensors 530 may be provided in series on the seat back 100 in a vertical direction.

The plurality of PCG sensors 530 are provided, and the control unit can derive a plurality of waveforms related to the PCG for respective PCG sensors 530, compare the maximum amplitude of a first cardiac sound with the magnitude of a noise signal for each waveform, and select a waveform, in which the maximum amplitude of a first cardiac sound is five times or more as large as that of the noise signal, as the representative PCG waveform.

Alternatively, a plurality of PCG sensors 530 are provided, and the control unit can derive a plurality of waveforms related to the PCG for respective PCG sensors 530, compare the maximum amplitude of a second cardiac sound with the magnitude of a noise signal for each waveform, and select a waveform, in which the magnitude of a second cardiac sound is three times or more as large as that of a noise signal, as the representative PCG waveform.

The PCG sensors are located on the backrest of the seat so as to record the sounds that occur when the valves of the heart open and close, and are each composed of a high-sensitive microphone and a sound collecting structure. Since the body shape of each person differs, a portion in which the seat back and the heart correspond to each other will differ, so that the PCG sensors are located on the backrest of the seat in the vertical direction. When PCG signals satisfy conditions in which the maximum amplitude of a first cardiac sound and the maximum amplitude of a second cardiac sound are respectively five times or more and three times or more as large as the noise level, the PCG signals are defined as high-quality signals, and an optimal PCG signal is selected from among the high-quality signals.

For reference, the PCG denotes a phonocardiogram, which is used to detect the period of the heart rate or analyze cardiac diseases by extracorporeally measuring sounds caused by vibrations occurring when the valves of the heart open and close. While the heart squeezes and pumps blood throughout the entire body when the mitral valve closes and the aortic valve opens, a first cardiac sound is generated. While new blood is coming into the left ventricle when the arterial blood flows out of the heart and then the mitral valve opens and the aortic valve closes, a second cardiac sound is generated.

Meanwhile, the heart rate sensors 500 may include PPG sensors 540. The PPG sensors 540 may be arranged at locations of the seat cushion 300, which come into contact with the thighs of the passenger.

A plurality of PPG sensors 540 can be provided, and the control unit can derive a plurality of waveforms related to the PPG for the respective PPG sensors 540, and select a waveform, in which a largest number of frequency components ranging from 0.5 to 2 Hz are present, from among the plurality of waveforms as the representative PPG waveform.

The PPG sensors are implemented using high-efficiency Light Emitting Diodes (LEDs) having near-infrared rays and red wavelength bands so as to take the PPG measurements while passing through the seat and clothes of the passenger, and are vertically configured such that they come into contact with the backs of the thighs of the passenger where there are relatively thick blood vessels. The PPG signals are subjected to Fast Fourier Transform (FFT), so that channels having a larger number of frequency components having a period of 0.5 to 2 Hz are defined as candidates for high-quality signals and then an optimal signal is selected after template matching has been performed using a basic PPG waveform.

For reference, the PPG is a method of measuring the waveform of blood using light because when the blood is periodically pumped out by the heart, the blood flows through blood vessels in the shape of a uniform wave. In this case, if the waveform is measured using two wavelength bands and measured values are compared, oxygen saturation in the blood can be measured.

FIG. 3 is a flowchart showing a method of observing the heart rate of a passenger according to various embodiments of the present invention. The method of observing the heart rate of a passenger according to the present invention includes the collection step S100 of collecting waveforms from a plurality of different types of heart rate sensors provided on a seat cushion or a seat back, for respective sensor types; the computing step S200 of computing accuracies of the waveforms for respective sensor types at each unit time; the selection step S300 of selecting a waveform having the highest accuracy at each unit time; and the calculation step S400 of calculating a heart rate based on the selected waveform.

In addition, the method may further include the step S500 of determining the physical condition or the like of the passenger using the calculated heart rate, and the step S600 of, after step S500, providing a service such as a warning using a voice, a motion or a touch, or a call to a hospital or a simple diagnosis.

As described above, the system and method for observing the heart rate of a passenger having the above configuration are advantageous in that for a plurality of different types of sensors and even for the same type of sensor, the most optimal signal among a plurality of signals is periodically evaluated and selected, thus reliably obtaining a relatively accurate heart rate.

For convenience in explanation and accurate definition in the appended claims, the terms lower, and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A system for observing a heart rate of a passenger, comprising:
   a plurality of different types of heart rate sensors provided on a seat cushion or a seat back; and
   a control unit for collecting waveforms of the heart rate sensors for respective sensor types, computing accuracies of the waveforms for respective sensor types at each unit time, selecting a waveform having a highest accuracy for each unit time, and then calculating a heart rate;
   wherein the heart rate sensors comprise electrocardiogram (ECG) sensors;
   wherein respective pairs of ECG sensors are provided on the seat back and the seat cushion;
   wherein the control unit configures a plurality of ECG measurement circuit leads by combining the plurality of ECG sensors, thus deriving a plurality of waveforms related to the ECG; and
   wherein the control unit measures magnitudes of an R-peak and a P-peak of each waveform related to the ECG, and selects a waveform, in which a magnitude of an R-peak is five times or more as large as that of a P-peak, as a representative ECG waveform.

2. A system for observing a heart rate of a passenger, comprising:
   a plurality of different types of heart rate sensors provided on a seat cushion or a seat back; and
   a control unit for collecting waveforms of the heart rate sensors for respective sensor types, computing accuracies of the waveforms for respective sensor types at each unit time, selecting a waveform having a highest accuracy for each unit time, and then calculating a heart rate;
   wherein the heart rate sensors comprise electrocardiogram (ECG) sensors;
   wherein respective pairs of ECG sensors are provided on the seat back and the seat cushion;
   wherein the control unit configures a plurality of ECG measurement circuit leads by combining the plurality of ECG sensors, thus deriving a plurality of waveforms related to the ECG; and
   wherein the control unit measures magnitudes of an R-peak and a T-peak of each waveform related to the ECG, and selects a waveform, in which a magnitude of an R-peak is three times or more as large as that of a T-peak, as a representative ECG waveform.

3. A system for observing a heart rate of a passenger, comprising:
   a plurality of different types of heart rate sensors provided on a seat cushion or a seat back; and
   a control unit for collecting waveforms of the heart rate sensors for respective sensor types, computing accuracies of the waveforms for respective sensor types at each unit time, selecting a waveform having a highest accuracy for each unit time, and then calculating a heart rate;
   wherein the heart rate sensors comprise ballistocardiogram (BCG) sensors; and
   wherein the BCG sensors include a plurality of BCG sensors, and the control unit derives a plurality of waveforms related to the BCG for respective BCG sensors, compares a magnitude of an I-J signal with a magnitude of a noise signal for each waveform, and selects a waveform, in which a magnitude of an I-J signal is seven times or more as large as that of a noise signal, as a representative BCG waveform.

4. The system of claim 3, wherein the BCG sensors are individually provided on the seat back and on the seat cushion.

5. A system for observing a heart rate of a passenger, comprising:
   a plurality of different types of heart rate sensors provided on a seat cushion or a seat back; and
   a control unit for collecting waveforms of the heart rate sensors for respective sensor types, computing accuracies of the waveforms for respective sensor types at each unit time, selecting a waveform having a highest accuracy for each unit time, and then calculating a heart rate;

wherein the heart rate sensors comprise phonocardiogram (PCG) sensors; and wherein the PCG sensors include a plurality of PCG sensors, and the control unit derives a plurality of waveforms related to the PCG for respective PCG sensors, compares a maximum amplitude of a first cardiac sound with a magnitude of a noise signal for each waveform, and selects a waveform, in which a maximum amplitude of a first cardiac sound is five times or more as large as that of a noise signal, as a representative PCG waveform.

6. The system of claim 5, wherein the PCG sensors are provided on the seat back.

7. The system of claim 5, wherein the PCG sensors include a plurality of PCG sensors in series on the seat back in a vertical direction.

8. A system for observing a heart rate of a passenger, comprising:

a plurality of different types of heart rate sensors provided on a seat cushion or a seat back; and a control unit for collecting waveforms of the heart rate sensors for respective sensor types, computing accuracies of the waveforms for respective sensor types at each unit time, selecting a waveform having a highest accuracy for each unit time, and then calculating a heart rate;

wherein the heart rate sensors comprise phonocardiogram (PCG) sensors; and wherein the PCG sensors include a plurality of PCG sensors are provided, and the control unit derives a plurality of waveforms related to the PCG for respective PCG sensors, compares a maximum amplitude of a second cardiac sound with a magnitude of a noise signal for each waveform, and selects a waveform, in which a maximum amplitude of a second cardiac sound is three times or more as large as that of a noise signal, as a representative PCG waveform.

9. A system for observing a heart rate of a passenger, comprising:

a plurality of different types of heart rate sensors provided on a seat cushion or a seat back; and a control unit for collecting waveforms of the heart rate sensors for respective sensor types, computing accuracies of the waveform for respective sensor types at each unit time, selecting a waveform having a highest accuracy for each unit time, and then calculating a heart rate;

wherein the heart rate sensors comprise photoplethysmogram (PPG) sensors; and wherein the PPG sensors include a plurality of PPG sensors are provided, and the control unit derives a plurality of waveforms related to the PPG for respective PPG sensors and selects a waveform having a largest number of frequency components ranging from 0.5 to 2 Hz, from among the plurality of waveforms, as a representative PCG waveform.

10. The system of claim 9, wherein the PPG sensors are provided in a portion of the seat cushion coming into contact with thighs of the passenger.

* * * * *